(12) United States Patent
Shio et al.

(10) Patent No.: US 7,842,648 B2
(45) Date of Patent: *Nov. 30, 2010

(54) AQUEOUS SUSPENDED AGRICULTURAL CHEMICAL COMPOSITION

(75) Inventors: Katsushi Shio, Funabashi (JP); Shoji Suzuki, Funabashi (JP); Naoki Matsumoto, Funabashi (JP)

(73) Assignee: Nissan Chemical Industries, Ltd., Tokyo (JP)

( * ) Notice: Subject to any disclaimer, the term of this patent is extended or adjusted under 35 U.S.C. 154(b) by 257 days.

This patent is subject to a terminal disclaimer.

(21) Appl. No.: 12/149,777

(22) Filed: May 8, 2008

(65) Prior Publication Data

US 2008/0220975 A1 Sep. 11, 2008

Related U.S. Application Data

(63) Continuation of application No. 09/446,730, filed as application No. PCT/JP98/02500 on Jun. 5, 1998, now abandoned.

(30) Foreign Application Priority Data

Jul. 11, 1997 (JP) ................................. 9-186553
Apr. 28, 1998 (JP) ................................ 10-118457

(51) Int. Cl.
*A01N 43/60* (2006.01)
(52) U.S. Cl. ................................................. 504/235
(58) Field of Classification Search .................... 504/235
See application file for complete search history.

(56) References Cited

U.S. PATENT DOCUMENTS 4,629,493 A 12/1986 Ura et al.
5,691,276 A * 11/1997 Ito et al. ..................... 504/134
6,664,213 B1 * 12/2003 Furusawa et al. ........... 504/215

FOREIGN PATENT DOCUMENTS

| EP | 0 103 171 A1 | 3/1984 |
|---|---|---|
| JP | A-56-39077 | 4/1981 |
| JP | A-57-203066 | 12/1982 |
| JP | A-2-214504 | 8/1990 |
| JP | B2-4-76721 | 12/1992 |
| JP | A-7-53526 | 2/1995 |

OTHER PUBLICATIONS

K. Miyake et al., *Crystallization Behaviors of α- and β-Quizalofop-ethyl Polymorphs in Homogeneous Nucleation*, ACS Symp. Ser., (1997) 667 (Separation and purification by crystallization), p. 101-110.
G. Sakata et al., *Preparation of optically pure ethyl(R)-(+) and (S)-(−)-2[4-(6-Chloro-2-quinoxalinyloxy)phenoxy]propanoate by resolution method and their herbicidal activities*, J. Pesticide Sci., (1985) 10(1) p. 75-79.
G. Sakata et al., *Synthesis and herbicidal activity of optically active ethyl 2-[4-(6-chloro-2-quinoxalinyloxy) phenoxy] propanoate*, J. Pesticide Sci., (1985) 10(1), p. 69-73.
A. Shiroishi et al., *Semi-batch cooling crystallization of quizalofop-ethyl with polymorphism*, ACS Symp. Ser., (1990) 438 (Cryst. Sep. process), p. 261-270.
K. Makino et al., *Crystal structure of a new herbicide, ethyl 2-[4-(6-chloro-2-quinoxalinyloxy) phenoxy] propanoate*, J. Pesticide Sci., (1986) 11(2), p. 237-243.

* cited by examiner

*Primary Examiner*—Alton N Pryor
(74) *Attorney, Agent, or Firm*—Oliff & Berridge, PLC

(57) ABSTRACT

The present invention relates to an aqueous suspended agricultural chemical composition wherein component (a) is ethyl(R)-2-[4-(6-chloroquinoxalin-2-yloxy)phenoxy]propionate of which the ratio of β-type crystal is 80% by weight or more, component (b) is surfactant and component (c) is water. An aqueous suspended agricultural chemical composition of the invention has good flowability and the growth of quizalofop-p-ethyl particle is small, resulting in high preservation stability under severe preservation condition.

14 Claims, No Drawings

AQUEOUS SUSPENDED AGRICULTURAL CHEMICAL COMPOSITION

This application is a continuation of U.S. application Ser. No. 09/446,730 filed Dec. 27, 1999, which is a National Stage application of PCT/JP98/02500 filed Jun. 5, 1998, and claims foreign priority to JP 10-118457 filed Apr. 28, 1998, and JP 9-186558 filed Jul. 11, 1997, the disclosures of which are incorporated herein by reference in their entirety.

BACKGROUND

1. Field of the Invention

The present invention relates to an aqueous suspended agricultural chemical composition having high preservation stability, which contains ethyl(R)-2-[4-(6-chloroquinoxalin-2-yloxy)phenoxy]propionate.

2. Description of the Related Art

Ethyl(R)-2-[4-(6-chloroquinoxalin-2-yloxy)phenoxy]propionate (hereinafter referred to as quizalofop-p-ethyl) is known to have two kinds of crystal forms. One is a low melting point type crystal (hereinafter referred to as α-type crystal) and the other is a high melting point type crystal (hereinafter referred to as β-type crystal) (see Japanese Patent Examined Publication No. Hei 4-76721).

Although quizalofop-p-ethyl has heretofore been handled as an emulsion, there is a demand for a highly safe aqueous suspended composition free of organic solvents (flowable agent). However when the aqueous suspended composition having been prepared with industrially produced α-type crystal quizalofop-p-ethyl particles is stored under severe condition, at 50° C. for 30 days, after the preparation, a phenomenon wherein flowability of this aqueous suspended composition deteriorates during the storage is sometimes observed. Therefore there has been a demand for the further improvement of the preservation stability the aqueous suspended composition.

SUMMARY OF THE INVENTION

As a result of an intensive study by the present inventors in order to solve the above-mentioned problem, there is found that an aqueous suspended agricultural chemical composition containing quizalofop-p-ethyl wherein the ratio of the β-type crystal is at least 80 wt % or more, a surfactant, and water, had extremely good preservation stability. Thus, the present invention is completed. That is, the present invention relates to [1] to [4] enumerated hereunder.

[1] An aqueous suspended agricultural chemical composition containing the following components (a), (b), and (c).

(a) Ethyl(R)-2-[4-(6-chloroquinoxalin-2-yloxy) phenoxy]propionate wherein the ratio of the β-type crystal is 80% by weight or more, (b) Surfactant, (c) Water.

[2] An aqueous suspended agricultural chemical composition described in the above item [1], wherein the component (a) is ethyl(R)-2-[4-(6-chloroquinoqunoxalin-2-yloxy phenoxy] propionate wherein the ratio of β-type crystal is 85% by weight or more.

[3] An aqueous suspended agricultural chemical composition as described in the above item [1], wherein the component (a) is Ethyl(R)-2-[4-(6-chloroquinoxalin-2-yloxy) phenoxy] propionate wherein the ratio of β-type crystal is 90% by weight or more.

[4] An aqueous suspended agricultural chemical composition as described in the above item [1] to [3], wherein the component (a) is 1 to 60 parts by weight, the component (b) is 0.1 to 60 parts by weight, and the component (c) is 20 to 95 parts by weight, respectively, based on 100 parts by weight of the aqueous suspended composition.

In quizalofop-p-ethyl used in the aqueous suspended agricultural composition of the present invention, the ratio of β-type crystal is at least 80% by weight or more, preferably 85% by weight or more, and more preferably 90% by weight or more in terms of the preservation stability of the agricultural chemical composition. If the ratio of β-type crystal is less than 80 wt %, the particle size of quizalofop-p-ethyl particle in the aqueous suspended agricultural chemical composition may increase (hereinafter referred to as particle growth) or flowability of the composition may deteriorate by storing the composition under severe condition such as at 50° C. for 30 days. The particle growth is not preferred in terms of herbicide effect and deteriorated flowability is not preferred in terms of the convenience of handling.

Quizalofop-p-ethyl is known to have two kinds of crystal forms. One is α-type crystal (low melting point type crystal), a plate crystal, of which endothermal peak is around 74° C. in differential scanning calorimetry, and the other is β-type crystal (high melting point type crystal), needle crystal, which endothermal peak is around 80° C.

These two crystal forms of quizalofop-p-ethyl are more easily discriminated each other through X-ray powder diffraction, differential scanning calorimetry, and microscopic observations.

Hereinafter, description is made of the characteristics of these two crystal forms.

|  | Melting point | Crystalline form | Characteristic X-ray diffraction peak |
|---|---|---|---|
| α-type crystal | 74 to 76° C. | Plate crystal | 2θ = 4.36, 8.68 |
| β-type crystal | 80 to 82° C. | Fine needle crystal | 2θ = 5.32, 6.38 |

As the weight ratio of α-type crystal to β-type crystal approximates to the area ratio of each endothermal peak in the differential scanning calorimetry, the weight ratio of α-type crystal to β-type crystal is obtained from the area ratio of the respective endothermal peaks.

The method of obtaining quizalofop-p-ethyl, in which the ratio of β-crystal is 80% by weight or more, is not specifically limited. For example, a method described in Japanese Patent Examined Publication No. Hei 4-76721 is suitably used in this invention. According to this method, quizalofop-p-ethyl containing β-type crystal at any ratio can be obtained.

Alternatively, quizalofop-p-ethyl may be replaced with diphenyl ether herbicide such as propaquizafop (general name), quizalofop-p-tefuryl (general name), fenoxaprop-ethyl (general name) in the invention. In this case, β-type crystal means high melting point type crystal and α-type crystal means low melting point type crystal.

Usable surfactant is not specifically limited and various anionic surfactants and nonionic surfactants heretofore used in agricultural chemical field are suitably used in the invention. Examples of surfactants are listed hereinafter. However surfactants suitably used in the invention are not limited to those listed therein.

Examples of anionic surfactants which can be suitably used in the invention include sulfonic acid surfactants, sulfate surfactants, phosphate surfactants and their salts. Examples of suitable sulfonic acid surfactants are alkylsulfonic acid, alkylolefinsulfonic acid, lignosulfonic acid, alkylbenzenesulfonic acid, alkylnaphthalenesulfonic acid, naphthalenesulfonic acid formaldehyde condensate, and dialkylsulfosuccinate. Examples of suitable sulfate surfactants are polyoxyethylene alkylether sulfate, polyoxyethylene alkyallylether sulfate, polyoxyethylene styrylphenylether sulfate, polyoxyethylene phenylalkylallylether sulfate, polyoxyalkylene glycol sulfate, higher alcohol sulfate, and fatty acid ester sulfate. Examples of suitable phosphate surfactants are polyoxyethylene alkylether phosphate, polyoxyethylene alkylallyl phosphate, polyoxyethylene phenylalkylallylether phosphate, higher alcohol phosphate, and polyoxyethylene tribenzylphenol phosphate. Example of their salts are sodium-, potassium-, magnesium-, calcium-, ammonium-, ethanolamine-, diethanolamine- and triethanol amine-salt.

Examples of suitable nonionic surfactants are polyoxyethylene alkylallyether, polyoxyethylene styrylphenylether, polyoxyethylene alkylether, polyoxyethylene phenylalkylallylether, polyoxyethylene sorbitan fatty acid ester, polyoxyethylene glycol, polyoxyethylene polyoxypropylene block co-polymer, polyoxyalkylene glycol, alkyne diol (acetylene glycol), alkynylene polyoxyethylenediol, sorbitan fatty acid ester and alkylallylether formaldehyde condensate and so forth.

These surfactants can be used separately or two kinds or more surfactants are allowed to be mixed. The mixing ratio can be freely selected.

In the aqueous suspended agricultural chemical composition of the present invention, content of quizalofop-p-ethyl in which the ratio of β-type crystal is 80% by weight or more, is not specifically limited, however it is generally 1 to 60 parts by weight, preferably 3 to 50 parts by weight to 100 parts by weight of the composition. Content of the surfactant is generally 0.1 to 60 parts by weight, preferably 0.3 to 50 parts by weight. Content of water is generally 20 to 95 parts by weight.

The composition of the invention can further contain following active components of agricultural chemicals.

Examples of the active components of agricultural chemicals suitably used in the invention include Diflufenican (general name), Propanil (general name), Dicamba (general name), Picloram (general name), 2,4-D (general name), 2,4-DB (general name), 2,4-DP (general name), Fluoroxypyr (general name), MCPA (general name), MCPP (general name), Triclopyr (general name), Diclofop-methyl (general name), Fenoxaprop-ethyl (general name), Fluazifop-butyl (general name), Haloxyfop-methyl (general name), Chloridazon (general name), Norflurazon (general name), Chlorpropham (general name), Desmedipham (general name), Phenmedipham (general name), Propham (general name), Alachlor (general name), Acetochlor (general name), Butachlor (general name), Metazachlor (general name), Metolachlor (general name), Pretilachlor (general name), Propachlor (general name), Oryzalin (general name), Pendimethalin (general name), Trifluralin (general name), Acifluorfen (general name), Bifenox (general name), Fluoroglycofen (general name), Fomesafen (general name), Halosafen (general name), Lactofen (general name), Oxyfluorfen (general name), Chlortoluron (general name), Diuron (general name), Fluometuron (general name), Isoproturon (general name), Linuron (general name), Metabenzthiazuron (general name), Lenacil (general name), Bromacil (general name), Imazapyr (general name), Imazaquin (general name), Imazethapyr (general name), Imazamethabenz (general name), Imazamox (general name), Alloxydim (general name), Clethodim (general name), Cycloxydim (general name), Sethoxdim (general name), Talkoxydim (general name), Bromoxynil (general name), Dichlobenil (general name), Ioxnil (general name), Mefenacet (general name), Amidosulfuron (general name), Bensulfuron-methyl (general name), Chlorimuron-ethyl (general name), Chlorsulfuron (general name), Cinosulfuron (general name), Metsulfuron-methyl (general name), Nicosulfuron (general name), Primisulfuron (general name), Prosulfuron (general name), Halosulfuron-methyl (general name), Thifensulfuron-methyl (general name), Triasulfuron (general name), Tribenuron-methyl (general name), Butylate (general name), Cycloat e (general name), Diallate (general name), EPTC (general name), Esprocarb (general name), Molinate (general name), Prosulfocarb (general name), Thiobencarb (general name), Triallate (general name), Atrazine (general name), Cyanazine (general name), Simazine (general name), Simetryne (general name), Terbutryn (general name), Terbutylazin (general name), Hexazinon (general name), Metamitron (general name), Metribuzin (general name), Aminotriazole (general name), Benfuresate (general name), Bentazon (general name), Cinmethylin (general name), Clomazone (general name), Clopyralid (general name), Difenzoquat (general name), Dithiopyl (general name), Ethofumasate (general name), Fluorochloridone (general name), Glufosinate (general name), Glyphosate (general name), Isoxaben (general name), Paraquat (general name), Pyridate (general name), Quinclorac (general name), Quinmerac (general name), Sulphosate (general name), Tridiphane (general name), Flumetsulam (general name), Fluthiacet-methyl (general name), Sulfentrazone (general name), Carfentrazone (general name), Dimethenamide (general name), Isoxaflutole (general name), Oxasulfuron (general name), Cloransulam-methyl (general name), Flumiclorac-pentyl (general name), Fluthiamide (general name), Aclonifen (general name), Benazolin (general name).

These active components of agricultural chemicals are used separately or two kinds or more of them are allowed to be mixed. The mixing rate can be freely selected. The amount of addition of the active components to the composition of the invention is properly selected. However, preferably, it is selected within 0.1 to 50 parts by weight.

Adjuvants suitably contained in the composition of this invention include thickeners, antifreezing agents, antifoaming agents, antibacterial and antifungal agents, and colorants, and the examples are cited as follows.

Thickeners suitably used in the composition of this invention are not specifically limited and include organic- and inorganic-natural materials and synthetic- and semisynthetic products. Examples of the thickeners suitably used in the invention include heteropolysaccharides, water soluble polymer compounds, cellulose derivatives, and smectite clay minerals. Examples of suitable heteropolysaccharides are xanthan gum, welan gum and rhamxan gum. Examples of suitable water soluble polymer compounds are polyvinylalcohol, polyvinylpyrrolidone, polyacrylic acid, sodium poly acrylate, and polyacrylamide. Examples of suitable cellulose derivatives are methylcellulose, carboxymethylcellulose, carboxyethylcellulose, hydroxyethylcellulose, and hydroxypropylcellulose. Examples of suitable smectite clay minerals are montmorillonite, saponite, hectorite, bentonite, raponite and synthetic smectite. These thickeners can be used separately or two kinds or more of them can be mixed and the ratio of the mixing can be selected freely.

Intact thickeners or those dispersed in water beforehand are allowed to be added. And the amount of the addition can be selected freely at its addition to the component of the invention.

Antifreezing agents may be used in the composition of this invention if required. As usable antifreezing agents, there may be added ethylene glycol, diethylene glycol, propylene glycol, or the like. The amount of the addition is freely selected at its addition to the composition of this invention.

Furthermore, antifoaming agent such as silicon emulsion, antibacterial and antifungal agents, and colorants are allowed to be blended. Various antibacterial and antifungal agents may be used in the invention. Example of suitable antibacterial and antifungal agents include benzoic acid and its salt, Proxel GXL (ICI Corp.) and Proxel XL-2 (ICI Corp.). Other than that, proper selection is made from various antibacterial and antifungal agents. And the amounts of addition can be freely selected at their addition to the composition of the invention.

The composition of the invention is, for example, prepared by a method in which the solid components contained in the composition of the invention is mixed into the water added and mixed with a surfactant, and then the mixture is subjected to atomization with a wet mill such as a sand grinder, and then, to the atomized mixture, other adjuvants such as a thickener is added and mixed.

DETAILED DESCRIPTION OF THE PREFERRED EMBODIMENT

Next, examples of the preparation of the composition of this invention and comparative examples of the aqueous mixtures of agricultural chemical compositions used for comparison are explained. "Part" used in examples and comparative examples means part by weight. Furthermore, this invention is not limited to these examples.

Example 1

1. Preparation of Ground Slurry 4.5 parts of Sorpol 3353 (mixture of polyoxyethylenestyrylphenylether and polyoxyethylene-polyoxypropylene block copolymer/Toho Chemical Industry, Product name), 0.15 parts of Antifoam E-20 (Silicone antifoaming agent/Kao Corp., Product name) were dissolved in 59.35 parts of water. 36 parts of quizalofop-p-ethyl (ratio of β-type crystal:100% by weight) was dispersed therein. Then the disperse solution was subjected to wet milling with a sand-grinder (AIMEX CO., Ltd.)
using 300 g of glass beads (1.0 to 1.5 mm in diameter) for 120 minutes at 2,000 rpm to obtain ground slurry. During the milling, temperature of cooling water was kept within 10 to 15° C., and temperature of the solution was kept within 10 to 20° C.

2. Preparation of Dispersion Medium 2.25 parts of Vangel (smectite clay mineral/thickener/R.T. VANDERBILT Corp., Product name), 0.14 parts of xanthan gum, and 0.14 parts of Proxycel GXL (ICI Corp., Product name) were dispersed in 67.48 parts of water in order of Vangel, xanthan gum and Proxycel GXL. Then 30 parts of propylene glycol is added therein to obtain a dispersion medium.

3. Preparation of an Aqueous Suspended Agricultural Chemical Composition

The above-mentioned ground slurry was mixed in the dispersion medium in the ratio of two to one to obtain a homogeneous aqueous suspended agricultural chemical composition.

4. Confirmation of the Crystalline Form of Quizalofop-p-Ethyl in the Aqueous Suspended Composition From the obtained aqueous suspended agricultural chemical composition, about 3 g of the composition was separated, and then it was suspended in about 60 ml of water. Then the suspension was subjected to a centrifugal separator (Kokusan Enshinki Corp., H-300 type, at 3,000 rpm for 15 minutes) and the formed supernatant was removed. Then the obtained precipitation was suspended in about 60 ml of water and subjected to the centrifugal separator again. This washing operation with water was repeated six times. The obtained precipitation was spread on a filter paper and then dried in a desiccator for about 20 hours. Then 3 to 5 mg of the dried material was weighed accurately and subjected to differential scanning calorimetry (Mac Science Corp. Differential scanning calorimeter 3100, heating rate=1° C. per minute, sampling every 0.3 second). From the area ratio of endothermal peak of α-type crystal to that of β-type crystal, ratio of β-type crystal in quizalofop-p-ethyl was found to be 100% by weight.

Examples 2 to 5

According to the process of Example 1, aqueous suspensions of agricultural chemical composition, in which the ratio of β-type crystal in quizalofop-p-ethyl is 80% by weight or more, were obtained (Example 2: 96 wt %, Example 3: 90 wt %, Example 4: 85 wt %, Example 5: 80 wt %).

Example 6

Example 1 was repeated using quizalofop-p-ethyl (ratio of β-type crystal:100% by weight) except that 4.5 parts of Soprophor FL (polyoxyethylene tristyrylphenylether phosphate/RHONE-POULENC Corp., Product name) was used in stead of 4.5 parts of Sorpol 3353 to prepare an aqueous suspended agricultural chemical composition. Ratio of β-type crystal in quizalofop-p-ethyl was 100% by weight in the obtained aqueous suspended agricultural chemical composition.

Example 7

1. Preparation of Ground Slurry 6.25 parts of propylene glycol, 3.75 parts of Sorpol 3353, and 0.13 parts of Nopco 8034L (Silicon antifoaming agent/San Nopco Limited, Product name) were dissolved in 43.62 parts of water. In this solution, 46.25 parts of quizalofop-p-ethyl (ratio of β-type crystal:100% by weight) was dispersed. Then the disperse solution was subjected to wet milling by a sand grinder using 300 g of glass beads (1.0 to 1.5 mm in diameter) at 2,000 rpm, for 120 minutes to obtain ground slurry. During the milling, temperature of cooling water was kept within 5 to 10° C., and the temperature of the solution was kept within 10 to 20° C.

2. Preparation of a Dispersion Medium 0.25 parts of rhamxan gum and 0.25 parts of Proxycel XL-2 (ICI Corp., Product name) were dispersed in 99.5 parts of water in order of rhamzan gum and Proxycel XL-2, to obtain a dispersion medium.

3. Preparation of an Aqueous Suspended Agricultural Chemical Composition

The above-mentioned ground slurry and dispersion medium were mixed in the ratio of 4 to 1 to obtain a homogeneous aqueous suspended agricultural chemical composition. The rate of β-type crystal in quizalofop-p-ethyl was 100% by weight in the obtained aqueous suspended agricultural chemical composition.

Example 8

According to the process of Example 7, an aqueous suspended agricultural chemical composition was obtained, in which a ratio of β-type crystal of quizalofop-p-ethyl was 96% by weight.

Example 9

1. Preparation of Ground Slurry 5.56 parts of propylene glycol, 3.33 parts of Sorpol 3353, and 0.11 parts of Nopco 8034L were dissolved in 35.44 parts of water. 55.56 parts of quizalofop-p-ethyl (ratio of β-type crystal:100% by weight) was dispersed in the solution. Dispersion solution was subjected to wet milling by a sand grinder using 300 g of glass beads (1.0 to 1.5 mm in diameter) at 2,000 rpm for 120 minutes to obtain ground slurry. During the milling, temperature of cooling water was kept within 5 to 10° C. and temperature of the solution was kept within 10 to 20° C.

2. Preparation of a Dispersion Medium 0.25 parts of welan gum and 0.25 parts of Proxel GXL were dispersed in order of Welan gum and Proxycel GXL, to obtain a dispersion medium.

3. Preparation of an Aqueous Suspended Agricultural Chemical Composition

The above-mentioned ground slurry and dispersion medium was mixed in the ratio of 9 to 1 to obtain a homogeneous aqueous suspended agricultural chemical composition. Ratio of β-type crystal of quizalofop-p-ethyl is 100% by weight in the obtained aqueous suspended agricultural chemical composition.

Comparative Examples 1 to 4

According to the process of Example 1, an aqueous mixture of agricultural chemical composition was obtained, in which ratio of β-type crystal in quizalofop-p-ethyl was less than 80% by weight (Comparative Example 1: 78 wt %, Comparative Example 2: 38 wt %, Comparative Example 3: 10 wt %, Comparative Example 4: 0 wt %).

Test Example

Particle size and viscosity of the aqueous suspended agricultural chemical composition obtained in Example 1 to 9, and in Comparative Example 1 to 4 were measured. Further, after they had been put in vials (inside volume 50 ml) respectively and stored in thermostatic chamber at 50° C. for 30 days, the particle size were measured.

1. Measurement of the Particle Size

Volume medium diameter (d50) values (μm) of the particles were measured with a Laser Diffraction Technique Particle Size Analyzer LS-130 (Coulter Corp.) using garnet. omd as an optical model.

2. Measurement of Viscosity

The viscosity was measured with a Viscometer DV-III (Brookfield Corp.) using No. 2 rotor at 30 rpm and 25° C.

Table 1 shows the result. The symbols in the Table have the following meanings.

A: A ratio (wt %) of β-type crystal of quizalofop-p-ethyl in the aqueous suspended composition.

B: Volume medium diameter (μ-m) of quizalofop-p-ethyl particle in the aqueous suspended composition immediately after preparation.

C: Viscosity (cps) of the aqueous suspended composition immediately after preparation.

D: Volume medium diameter (μ-m) of the particle in the aqueous suspended composition after 30 days storage at 50° C.

E: Viscosity (cps) of the aqueous suspended composition after 30 days storage at 50° C.

TABLE 1

|  | A | B | C | D | E |
|---|---|---|---|---|---|
| Example 1 | 100 | 1.3 | 180 | 1.9 | 248 |
| Example 2 | 96 | 1.4 | 213 | 1.8 | 321 |
| Example 3 | 90 | 1.2 | 167 | 2.0 | 252 |
| Example 4 | 85 | 1.3 | 216 | 2.2 | 279 |
| Example 5 | 80 | 1.3 | 193 | 2.4 | 332 |
| Example 6 | 100 | 1.1 | 178 | 1.6 | 232 |
| Example 7 | 100 | 1.0 | 202 | 1.7 | 185 |
| Example 8 | 96 | 1.2 | 227 | 1.6 | 178 |
| Example 9 | 100 | 1.3 | 451 | 2.1 | 337 |
| Comparison 1 | 78 | 1.2 | 178 | 4.3 | >1000 |
| Comparison 2 | 38 | 1.4 | 201 | 5.8 | >1000 |
| Comparison 3 | 10 | 1.1 | 194 | 4.9 | >1000 |
| Comparison 4 | 0 | 1.2 | 225 | 5.2 | >1000 |

B and C show physical properties immediately after preparation.

D and E show properties after 30 days storage at 50° C.

Above Table shows that, if the ratio of β-type crystal of quizalofop-p-ethyl is 80% by weight or more, the preservation stability of the aqueous suspended composition was high.

Because the Table shows that, even after severe storage condition, 50° C. for 30 days, the flowability was kept well making the composition convenient to handle and the growth of quizalofop-p-ethyl particle was small making the herbicidal activity high.

Effect of the Invention

An aqueous suspended agriculture chemical composition in the invention maintains good flowability and the growth of the quizalofop-p-ethyl particle is small, resulting in high preservation stability of the compositions under severe preservation condition.

What is claimed is:

1. A method for improving preservation stability of an aqueous suspended agricultural chemical composition, comprising:

adding ethyl(R)-2-[4-(6-chloroquinoxalin-2-yloxy)phenoxy]propionate, wherein at least 80%, by weight, of the ethyl(R)-2-[4-(6-chloroquinoxalin-2-yloxy)phenoxy]propionate is present in a β-type crystal form;
adding surfactant; and
adding water.

2. The method according to claim 1, wherein at least 85%, by weight, of the ethyl(R)-2-[4-(6-chloroquinoxalin-2-yloxy)phenoxy]propionate is present in the β-type crystal form.

3. The method according to claim 1, wherein at least 90%, by weight, of the ethyl(R)-2-[4-(6-chloroquinoxalin-2-yloxy)phenoxy]propionate is present in the β-type crystal form.

4. The method according to claim 1, wherein based on 100 parts by weight of the aqueous suspended agricultural chemical composition
the ethyl(R)-2-[4-(6-chloroquinoxalin-2-yloxy)phenoxy]propionate is 1 to 60 parts by weight,
the surfactant is 0.1 to 60 parts by weight, and
the water is 20 to 95 parts by weight.

5. The method according to claim 1, further comprising:
preparing particles comprising the ethyl(R)-2-[4-(6-chloroquinoxalin-2-yloxy)phenoxy]propionate, the particles having a volume medium diameter of from 1.0 to 1.4 μm.

6. The method according to claim 1, further comprising:
mixing the ethyl(R)-2-[4-(6-chloroquinoxalin-2-yloxy)phenoxy]propionate, the surfactant, and the water to form a disperse solution; and
preparing particles comprising the ethyl(R)-2-[4-(6-chloroquinoxalin-2-yloxy)phenoxy]propionate by subjecting the disperse solution to wet milling, the particles having a volume medium diameter of from 1.0 to 1.4 μm.

7. The method according to claim 5, wherein the volume medium diameter of the particles comprising the ethyl(R)-2-[4-(6-chloroquinoxalin-2-yloxy)phenoxy]propionate is from 1.6 to 2.4 μm after being stored at 50° C. for 30 days.

8. The method according to claim 6, wherein the volume medium diameter of the particles comprising the ethyl(R)-2-[4-(6-chloroquinoxalin-2-yloxy)phenoxy]propionate is from 1.6 to 2.4 μm after being stored at 50° C. for 30 days.

9. The method according to claim 1, further comprising:
mixing the ethyl(R)-2-[4-(6-chloroquinoxalin-2-yloxy)phenoxy]propionate, the surfactant, and the water with a dispersion medium to form a homogeneous aqueous suspended agricultural chemical composition having a viscosity of from 178 to 451 cps.

10. The method according to claim 1, further comprising:
mixing the ethyl(R)-2-[4-(6-chloroquinoxalin-2-yloxy)phenoxy]propionate, the surfactant, and the water to form a disperse solution;
preparing particles comprising the ethyl(R)-2-[4-(6-chloroquinoxalin-2-yloxy)phenoxy]propionate by subjecting the disperse solution to wet milling, the particles having a volume medium diameter of from 1.0 to 1.4 μm;
mixing the disperse solution with a dispersion medium to form a homogeneous aqueous suspended agricultural chemical composition having a viscosity of from 178 to 451 cps.

11. The method according to claim 9, wherein the viscosity of the homogeneous aqueous suspended agricultural chemical composition is from 178 to 337 cps after being stored at 50° C. for 30 days.

12. The method according to claim 10, wherein the viscosity of the homogeneous aqueous suspended agricultural chemical composition is from 178 to 337 cps after being stored at 50° C. for 30 days.

13. The method according to claim 10, wherein the volume medium diameter of the particles comprising the ethyl(R)-2-[4-(6-chloroquinoxalin-2-yloxy)phenoxy]propionate is from 1.6 to 2.4 μm after being stored at 50° C. for 30 days.

14. The method according to claim 10, wherein the viscosity of the homogeneous aqueous suspended agricultural chemical composition is from 178 to 337 cps after being stored at 50° C. for 30 days; and the volume medium diameter of the particles comprising the ethyl(R)-2-[4-(6-chloroquinoxalin-2-yloxy)phenoxy]propionate is from 1.6 to 2.4 μm after being stored at 50° C. for 30 days.

* * * * *